United States Patent [19]
Chen

[11] Patent Number: 5,893,055
[45] Date of Patent: Apr. 6, 1999

[54] TWO-DIMENSIONAL WEB PROPERTY VARIATION MODELING AND CONTROL

[75] Inventor: Shih-Chin Chen, Dublin, Ohio

[73] Assignee: ABB Industrial Systems, Inc., Columbus, Ohio

[21] Appl. No.: 865,717

[22] Filed: May 30, 1997

[51] Int. Cl.[6] ............................ G06F 17/00; G05B 13/00
[52] U.S. Cl. ................ 702/189; 364/471.02; 364/471.03
[58] Field of Search ............................... 364/560, 471.01, 364/471.02, 471.03, 177, 158; 162/252, 253, 254, 259, 263; 73/73, 159; 702/189

[56] References Cited

U.S. PATENT DOCUMENTS

| | | | |
|---|---|---|---|
| 3,767,900 | 10/1973 | Chao et al. | 364/471.03 |
| 3,852,578 | 12/1974 | Rice | 364/471.03 |
| 4,453,404 | 6/1984 | Powell et al. | 364/471.03 |
| 4,707,779 | 11/1987 | Hu | 364/471.03 |
| 4,910,688 | 3/1990 | Amini | 364/471.03 |
| 4,939,929 | 7/1990 | Östman | 364/471.03 |
| 4,965,736 | 10/1990 | Balakrishnan | 364/471.03 |
| 4,982,334 | 1/1991 | Balakrishnan | 364/471.03 |
| 5,071,514 | 12/1991 | Francis | 162/259 |
| 5,122,963 | 6/1992 | Chen | 364/471.03 |
| 5,563,809 | 10/1996 | Williams et al. | 364/560 |
| 5,583,782 | 12/1996 | Heaven et al. | 364/471.03 |

OTHER PUBLICATIONS

"Wavelet Analysis" Bruce, Donoho & Gao—IEEE Spetrum, Oct. 1996, pp. 26–35.

"Orthogonal Functions for Cross–directional Control of Web Forming Processes" by W.P. Heath, Automatica vol. 32, No. 2, pp. 183–198, 1996.

"Cross–directional Control on Paper Machines using Gram Polynomials" by Kristinn Kristinsson and Guy A. Dumont, Automatica, vol. 32, No. 4, pp. 533–548, 1996.

Primary Examiner—John Barlow
Assistant Examiner—Bryan Bui
Attorney, Agent, or Firm—Killworth, Gottman, Hagan & Schaeff, L.L.P.

[57] ABSTRACT

A new two-dimensional (2D) variation modeling and control technique for a machine producing a web of material, such as paper, uses functional transformation with basis functions which are wavelets, preferably wavelets derived from and closely resembling the responses generated by actuation of cross direction (CD) actuators of the machine. By using the disclosed functional transformation together with carefully selected basis functions, memory and real-time processing requirements are substantially reduced so that practical controls can be readily implemented. In addition, the functional transformation technique of the present application expands conventional CD correction to also correct for a portion of the residual variations which, until now, have remained uncorrected. The new 2D profile is treated as the superposition of two main components: a pure machine direction (MD) variation component and a two-dimensional sheet variation component. The pure MD variation is identical to the conventional MD variation; however, the two-dimensional sheet variation represents the evolution of a sheet property being measured in both a temporal direction (TD) and a spatial direction (SD), i.e. it includes both the traditional pure CD profile and a portion of the residual variation. The TD is aligned with the MD and the SD is perpendicular to the TD or is aligned with the CD. The new 2D variation is controlled by a new 2D control arrangement which includes an optimal predictive SD controller and a model based TD controller to quickly achieve 2D web uniformity.

25 Claims, 8 Drawing Sheets

TWO-DIMENSIONAL WEB PROPERTY VARIATION MODELING AND CONTROL

BACKGROUND OF THE INVENTION

The present invention relates in general to web forming processes and, more particularly, to improved two-dimensional web property variation by means of modeling web property variations using functional transformation and controlling web property variations with two-dimensional optimal predictive controllers. "Dimensional" as used herein refers to the number of independent variables such that if a dependent variable y is plotted versus an independent variable x, the plot will be referred to as one-dimensional; if a dependent variable z is plotted versus two independent variables x and y, the plot will be referred to as two-dimensional; and so forth.

Machines and processes which produce webs of sheet material, such as paper, plastic and aluminum, encounter common control problems in producing webs which satisfy required specifications for characteristics for a given product. Specifications commonly include required ranges for thickness, moisture content, weight per unit area, smoothness and the like. Quality control is complicated by the fact that characteristics vary in both the machine direction (MD) or direction of movement of the web through a machine as it is being produced and in the machine cross direction (CD) or lateral direction across the machine or web.

The MD variations in the web are affected by factors which impact the entire width of the web including, for example, the source of materials being used to form the web, other common supplies used to produce the web such as steam, the speed of the machine producing the web, and other similar factors. On the other hand, CD variations are controlled by arrays of actuator devices which are distributed across the width of the machine producing the web. On paper making machines, for which the present invention is particularly applicable and initially being applied, the CD actuator devices include slice lip actuators which are adjusted to control the slice of a headbox, dilution valves, steam showers, heaters, calenders, and other known devices.

Cross-direction (CD) profile control has been used to improve CD uniformity in many web forming processes including paper making machines, as well as plastic film extruders, sheet calenders, coaters and similar machines. Due to the speed and resolution limits of web scanning measurements, CD control actions are usually applied infrequently. Thus, long term or steady-state CD profile uniformity has been generally satisfactory in existing CD control arrangements.

However, there is a growing demand for better short-term profile uniformity in many sheet-making processes. One example of this demand in the paper making industry is the desire to produce uniform and sellable paper almost immediately after any process transition such as machine start-up, product grade change, sheet break recovery, and the like. The demand for more responsive web uniformity has also intensified due to the arrival of new stationary full-width sheet property measurement, see U.S. Pat. No. 5,563,809 which is incorporated herein by reference. Unfortunately, existing CD profile control arrangements can not satisfy this demand due to the massive amounts of memory and real-time processing required.

A new control technique is thus needed to satisfy these demands and to make sheet-forming processes achieve true two-dimensional uniformity responsively. Preferably, the new control technique would correct conventional CD variations and also some residual variations which previously have gone uncorrected.

SUMMARY OF THE INVENTION

This need is met by the invention of the present application wherein a new variation modeling and control technique for a machine producing a web of material, such as paper, uses functional transformation with basis functions which are wavelets, preferably wavelets derived from and closely resembling the responses generated by actuation of cross direction (CD) actuators of the machine. By using the disclosed functional transformation and carefully selecting the basis functions, the present invention substantially reduces the memory and real-time processing requirements so that practical controls can be readily implemented. In addition, the functional transformation technique of the present application expands conventional CD control arrangements to also correct for a portion of the residual variations which, until now, has largely remained uncorrected.

In the invention of the present application, a measured profile is treated as the superposition of two main components: a pure MD variation component and a two-dimensional (2D) sheet variation component. The pure MD variation component is identical to conventional MD variation; however, the two-dimensional sheet variation represents the evolution of a sheet property being measured in both a temporal direction (TD) and a spatial direction (SD), i.e. it includes both the traditional pure CD variation or profile and a portion of residual variation. The temporal direction is aligned with the machine direction (MD) and the spatial direction (SD) is perpendicular to the temporal direction or is aligned with the machine cross direction (CD). TD and SD are introduced to define the two-dimensional sheet variation and to distinguish the two-dimensional sheet variation from the traditional CD profiles which are typically estimated from scanning sensors.

For use in a paper making machine, the web of paper being produced is monitored, preferably by a full-width stationary monitoring system which generates a profile signal or measurement function. After the conventional machine direction (MD) variations are removed from the profile signal or measurement function, the resulting two-dimensional sheet variation signal is transformed by convoluting the two-dimensional sheet variation signal with basis functions the same as or preferably derived from the responses which are generated when CD actuators of the machine are controlled or actuated. The resulting transformation is combined with a functional transformation of a target or reference profile function with the resulting transformation being processed in transform space by an optimal predictive spatial direction (SD) variation controller. The output of the SD variation controller is used directly as an input signal for a model predictive temporal direction (TD) variation controller. The output of the TD variation controller is fed to a deadtime delay coordinator which unifies the delay time differences encountered among the responses of the CD actuators. The output of the deadtime delay coordinator is fed back through a profile TD response model and may be filtered to serve as a positive feedback input to the TD controller. The TD variation controller, the deadtime coordinator, the profile TD response model and the feedback filter, if used, form an inner control loop which takes the output from the SD variation controller as its input and generates a process control signal for CD actuators of the machine producing the web of material. The resulting process control signal is used to perform two-dimensional control of the process. Thus, the control arrangement of the present invention corrects for not only conventional CD variations but also for residual variations such that a true two-dimensional correction is performed.

In accordance with one aspect of the present invention, a method for determining a two-dimensional variation for a web of material as the web of material is being manufactured comprises measuring at least one characteristic of the web substantially across an entire width of the web to generate a two-dimensional measurement function. A series of wavelet basis functions is then selected and the two-dimensional measurement function is then convoluted with the wavelet basis functions to generate a two-dimensional variation signal representative of the web of material. The step of selecting a series of wavelet basis functions preferably comprises determining response profiles generated in response to actuations of CD actuators used in a machine performing the method, and deriving the series of wavelet basis functions from the response profiles. Alternately, the step of selecting the series of wavelet basis functions may comprise determining response profiles generated in response to actuations of CD actuators used in a machine performing the method, and to selecting the series of wavelet basis functions to closely match the response profiles. The wavelet basis functions can be either wavelet scaling basis functions or wavelet detail basis functions; however, the scaling basis functions are used for control of CD variations while detail basis functions are used for analysis of CD variations.

In accordance with another aspect of the present invention, a method for determining a two-dimensional variation for a web of material as the web of material is being manufactured along a machine direction comprises measuring at least one characteristic of the web of material as a function of the cross machine direction of the web of material to generate a measurement function. A determination of the variation in the machine direction of the web of material which is substantially independent of the cross machine direction is made and used to generate a pure machine direction function. The pure machine direction function is then separated from the measurement function to generate a two-dimensional sheet variation function. Using wavelet basis functions to transform the two-dimensional sheet variation function into a two-dimensional variation signal representative of the web of material.

The step of separating the pure machine direction function from the measurement function may comprise subtracting the pure machine direction function from the measurement function. The transformation of the two-dimensional sheet variation function may comprise selecting a series of wavelet basis functions, and convoluting the two-dimensional sheet variation function with the wavelet basis functions to generate a two-dimensional variation signal representative of the web of material.

In accordance with yet another aspect of the present invention, a method for controlling a two-dimensional variation for a web of material as the web of material is being manufactured comprises measuring at least one characteristic of the web substantially across an entire width of the web to generate a measurement function. Determining a two-dimensional measurement function from said measurement function and transforming said two-dimensional measurement function to generate a transformed variation expression representative of the web of material. A reference profile function is determined and the reference profile function is transformed to generate a transformed reference expression representative of the reference profile function. Subtracting said transformed variation expression from said transformed reference expression to generate a first input signal for a spatial direction controller. A spatial direction control signal is generated in response to the first input signal. The spatial direction control signal is combined with a modeled temporal direction feedback signal to generate a second input signal for a temporal direction controller. A process control signal is generated in response to the second input signal and deadtime delays are coordinated to unify delay times among a series of cross direction actuators to generate a process control signal.

The method may further comprise the step of configuring the spatial direction controller to be an optimal predictive spatial direction controller. The step of transforming the measurement function to generate a transformed variation expression representative of the web of material may comprise the steps of selecting a series of wavelet scaling basis functions, and convoluting the two-dimensional measurement function with the wavelet scaling basis functions. The step of selecting a series of wavelet basis functions preferably comprises determining response profiles generated in response to actuations of CD actuators used in a machine performing the method and deriving the series of wavelet scaling basis functions from the response profiles. The step of transforming the reference profile function to generate a reference transform expression representative of the profile function may comprise convoluting the reference profile function with the series of wavelet scaling basis functions.

In accordance with still another aspect of the present invention, a method for controlling a two-dimensional variation of a web of paper as the web of paper is being manufactured by a paper making machine having a headbox actuator comprises measuring at least one characteristic of the web substantially across an entire width thereof to generate a measurement function. Machine direction variations contained within the measurement function are determined and removed from the measurement function to generate a two-dimensional variation signal including both cross directional and residual variations. The headbox actuator is then controlled in response to the two-dimensional variation signal. The step of controlling the headbox actuator may comprise the step of controlling a slice lip of the headbox or controlling a dilution valve of the headbox.

The method may further comprise transforming the two-dimensional measurement function to generate a transformed variation expression representative of the web of material. A reference profile function is determined and transformed to generate a transformed reference expression representative of the reference profile function. The transformed variation expression and transformed reference expression are combined to generate a first input signal for a spatial direction controller which generates a spatial direction control signal in response to the first input signal. The spatial direction control signal is combined with a modeled temporal direction feedback signal to generate a second input signal for a temporal direction controller which generates a two-dimensional process control signal in response to the second input signal. Deadtime delay coordination is performed to unify delay times among a series of cross direction actuators to generate a process control signal from the two-dimensional process control signal.

The temporal controller includes an adjustable closed-loop time constant and the method may further comprise filtering the two-dimensional measurement function with a filter having an adjustable filter time constant and filtering the modeled temporal direction feedback signal with a filter having an adjustable filter time constant. The adjustable filter time constants and closed loop time constants are adjusted to control two degrees of freedom of two-dimensional variation control of the method, with the first and second time constants being adjusted to be substantially equal to one another. Adjustment of the filter time constants adapting the method to different two-dimensional variations and adjustment of the closed loop time constant adapting the method to changes of the reference profile function.

In accordance with an additional aspect of the present invention, a method for controlling a two-dimensional variation of a web of material as the web of material is being manufactured by a machine having a cross direction controller comprises measuring at least one characteristic of the web substantially across an entire width of the web to generate a measurement function. Machine direction variations contained within the measurement function are determined and removed from the measurement function to generate a two-dimensional variation signal including both cross directional variations and residual variations. The cross direction controller is then controlled in response to the two-dimensional variation signal. The step of controlling the cross direction controller may comprise selecting a series of wavelet basis functions, and decomposing the two-dimensional variation signal using the basis functions. The step of selecting the basis functions may comprise selecting the basis functions to be wavelet scaling basis functions. Preferably, the selection of a series of wavelet basis functions comprises determining response profiles generated in response to actuations of CD actuators of the cross direction controller, and deriving the series of wavelet basis functions from the response profiles.

It is, thus, an object of the present invention to provide an improved method for controlling manufacture of a web of material by controlling two-dimensional variation in a web of material as it is being manufactured; to provide improved two-dimensional modeling, control and analysis techniques for machines used to produce webs of material such as paper; to provide improved two-dimensional modeling, control and analysis for machines used to manufacture webs of material such as paper using transformation of signals generated for control of the machines using wavelet basis functions; and, to provide improved two-dimensional modeling, control and analysis for machines used to manufacture webs of material such as paper using transformation of signals generated for control of the machines using wavelet basis functions which are based on response characteristics of cross direction actuators of the machines.

Other objects and advantages of the invention will be apparent from the following description, the accompanying drawings and the appended claims.

DETAILED DESCRIPTION OF THE INVENTION

While the present invention is generally applicable to a wide variety of web forming processes such as plastic film extruders, sheet calenders and coaters, it will be described herein with reference to a paper making machine for which it is particularly applicable and is being initially applied. Further, while the invention preferably utilizes a full width monitoring system such as the one disclosed in referenced U.S. Pat. No. 5,563,809, other forms of sensors including more conventional scanning sensors and dry-line sensors can be used in the present invention.

The invention of the present application enables modeling, control and analysis of a two-dimensional sheet property variation in a web-forming process. As a broad overview of the present invention, a web being manufactured is monitored to generate a measurement function or profile signal. A machine direction (MD) variation component of that profile signal is determined and removed from the profile signal to generate a two-dimensional signal. The two-dimensional signal includes conventional cross direction (CD) variations and also residual variations which, until now, have not been effectively modeled and controlled. The two-dimensional signal is processed so that it can be used to control CD actuators of a cross direction controller of the web forming machine, such as dilution valves and/or slice actuators of a headbox of a paper making machine. Thus, two-dimensional control of web variations are accomplished via conventional one dimensional actuators or CD actuators. The two-dimensional signal or function is processed using functional transformation to permit the disclosed control arrangement to be implemented in practical control systems for web forming machines.

The theory of operation of the invention of the present application will now be described. Initially, let p(x,t) represent a web property, such as basis weight, of a sheet of paper measured at a machine cross direction (CD) location x and at time t, where $0 \leq x \leq w$ and $t_o \leq t \leq t_f$. The bold letter p(x,t) represents the full-width sheet property variation as a function of full-width variable x and time t. Traditionally, p(x,t) is separated into three components, pure machine direction (MD) variation, pure CD variation (or profile), and residual variation for a given time interval ($t_o \leq t \leq t_f$). Pure MD variation at time t is the average of property p(x,t) for the entire CD width ($0 \leq x \leq w$). Pure CD profile is the average of p(x,t) over $t_o \leq t \leq t_f$ for each CD location x. The residual variation is whatever is left from the above separation.

In the novel two-dimensional (2D) profile processing approach of the present application, p(x,t) is treated as the superposition of two main components: the pure MD variation and a two-dimensional sheet variation. The pure MD variation is identical to the MD variation in the traditional definition, however, the two-dimensional sheet variation represents the evolution of a sheet property being measured in both a temporal direction (TD) and a spatial direction (SD) i.e. it includes both the traditional pure CD profile and a portion of the residual variation. The temporal direction is aligned with the machine direction (MD) and the spatial direction (SD) is perpendicular to the temporal direction or is aligned with the machine cross direction (CD). TD and SD are introduced to define the two-dimensional sheet variation and to distinguish the two-dimensional sheet variation from the traditional CD profiles which are typically estimated from scanning sensors.

The two-dimensional sheet property variation is different from the traditional CD variation in the sense that the two-dimensional sheet variation reflects the sheet variation at each SD point in the temporal direction. Two-dimensional sheet variation can also be seen as the continuous evolution of the entire SD profile in the temporal direction. The terms 2D variations and 2D profiles are used herein interchangeably with two-dimensional sheet property variation. The variation $y(x_y,t)$ at an SD location $x_y$ is called the TD variation of a 2D variation at $x_y$. The full profile function $y(x,t_k)$ at time $t_k$, is called the SD variation of a 2D variation at time $t_k$.

Mathematically, the pure MD component or pure machine direction variation function is the integration of p(x,t) for the entire range of x, i.e. across the entire width of the web from 0 to w, using the equation:

$$p(t) = \frac{1}{w} \int_0^w p(x,t) dt \quad (1)$$

The two-dimensional sheet property variation y(x,t) or two-dimensional measurement function is the difference between the full-width sheet property p(x,t) and the pure MD component p(t):

$$y(x,t) = p(x,t) - p(t)1(x) \quad (2)$$

where the function 1(x) is equal to one for all $0 \leq x \leq w$ and zero elsewhere.

Conceptually, the 2D sheet property variation y(x,t) can be further expressed as the combination of two key components, the variation $y_c(x,t)$ which results from CD control actions and the random variations d(x,t):

$$y(x,t) = y_c(x,t) + d(x,t) \quad (3)$$

Typically, the goal of a 2D sheet variation control is to make the 2D sheet property variation y(x,t) match with a 2D target or reference $y_r(x,t)$ as closely as possible. This goal is ultimately achieved by applying control actions to CD actuators to affect y(x,t) through changes of $y_c(x,t)$. It is very common, but not always necessary, that $y_r(x,t)$ be a flat profile or zero for all SD locations x.

In the invention of the present application, the two-dimensional sheet property variations y(x,t), $y_c(x,t)$, and $y_r(x,t)$ are treated as linear combinations of a set of basis functions. In general, the basis functions can be a variety of functions, for example orthogonal polynomials, windowed sinusoidal functions, principal components from the principal component analysis, wavelet functions, or combinations of these different bases. The inventor of the present application has determined that wavelet functions, including both scaling and detail basis functions, are particularly suited for performing 2D sheet variation modeling and control. As an example, a set of biorthogonal wavelet bases or basis functions are illustrated in FIGS. 1A–1D and a set of orthogonal wavelet bases or basis functions are shown in FIGS. 1E and 1F.

Figure 1A:
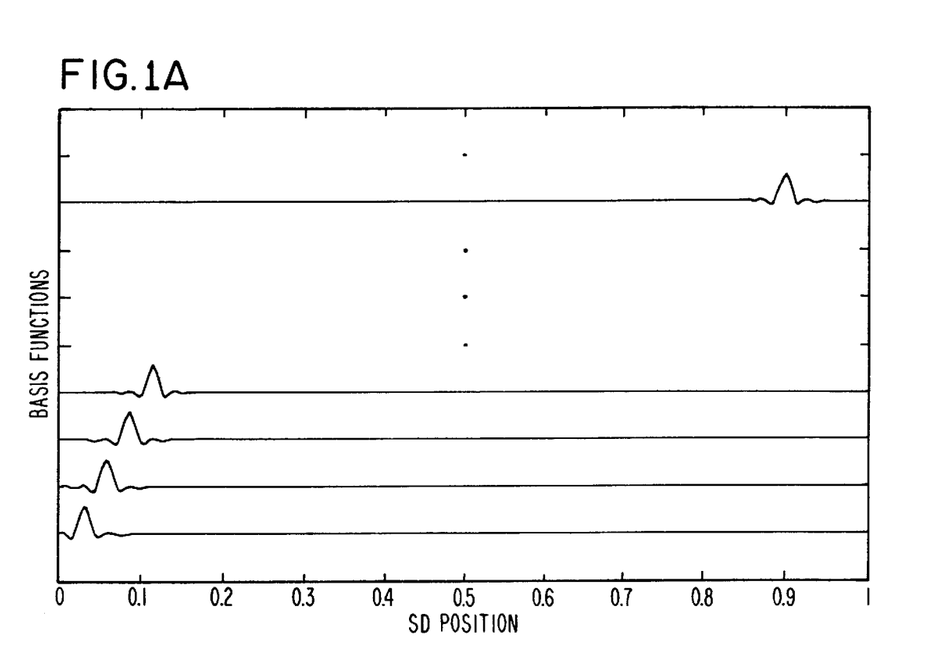
FIGS. 1A–1D illustrate a set of biorthogonal wavelets which can be used as basis functions in the present invention for both control and analysis purposes.
Figure 1B:
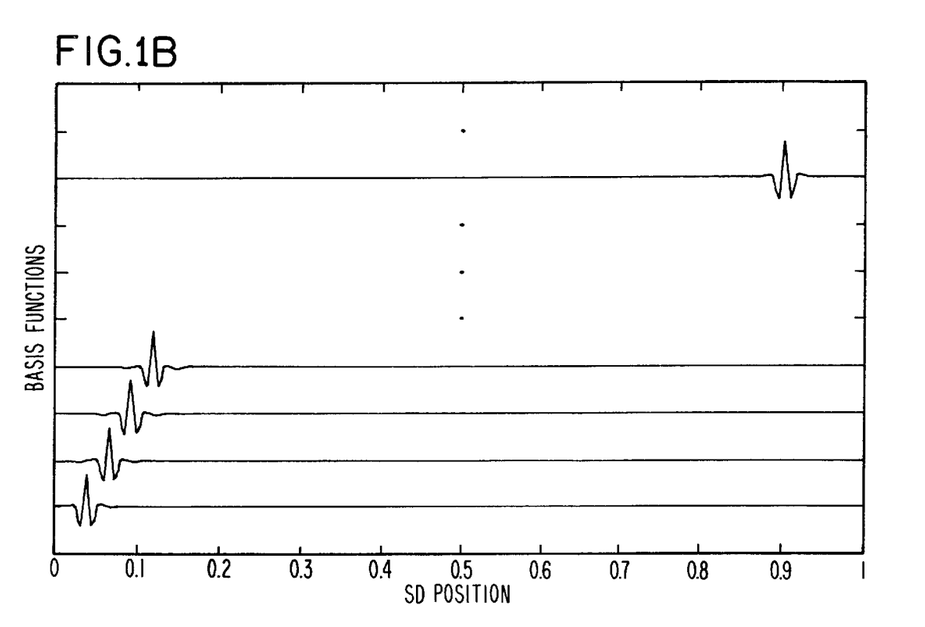
Figure 1C:
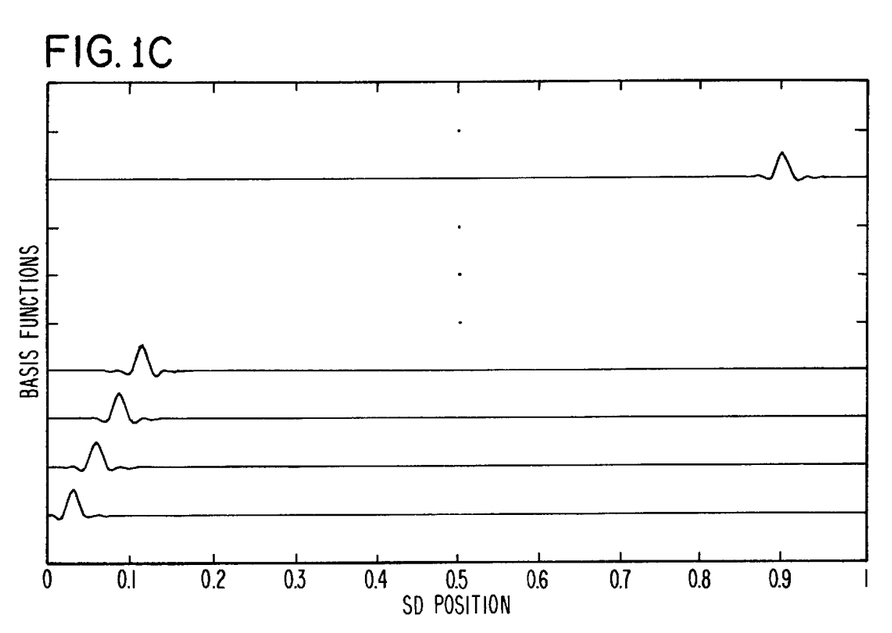
Figure 1D:
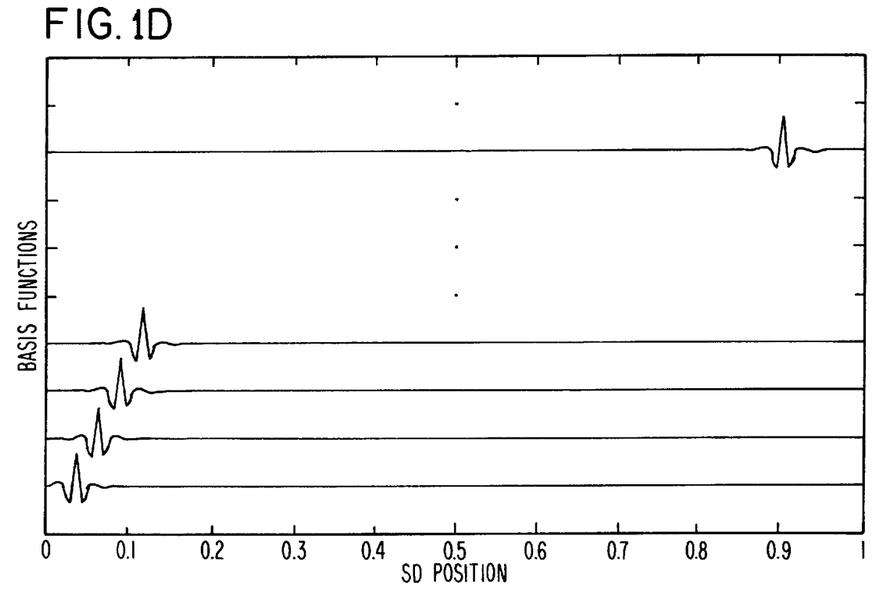
Figure 1E:
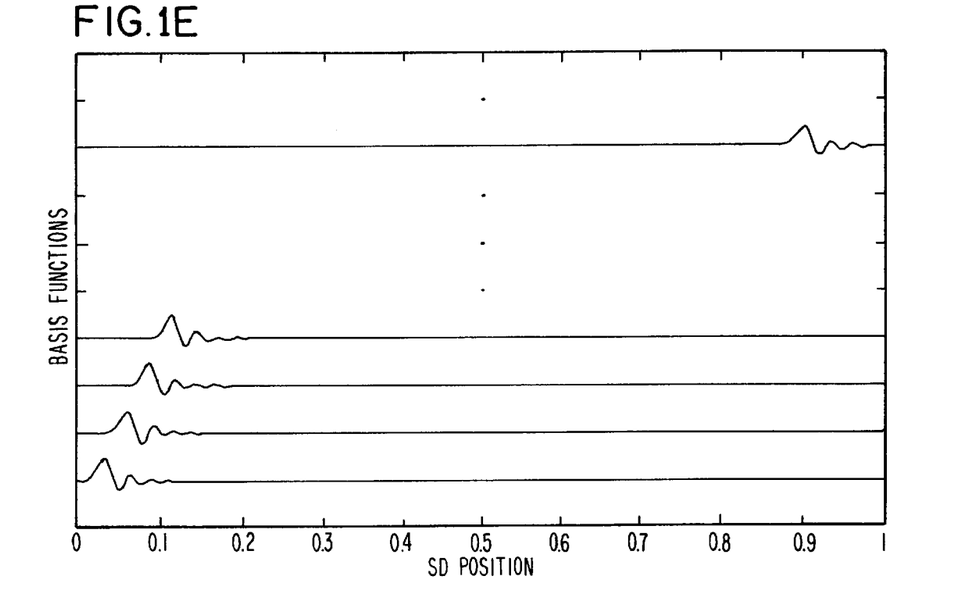
FIGS. 1E and 1F illustrate a set of orthogonal wavelets which can be used as basis functions in the present invention for both control and analysis purposes.
Figure 1F:
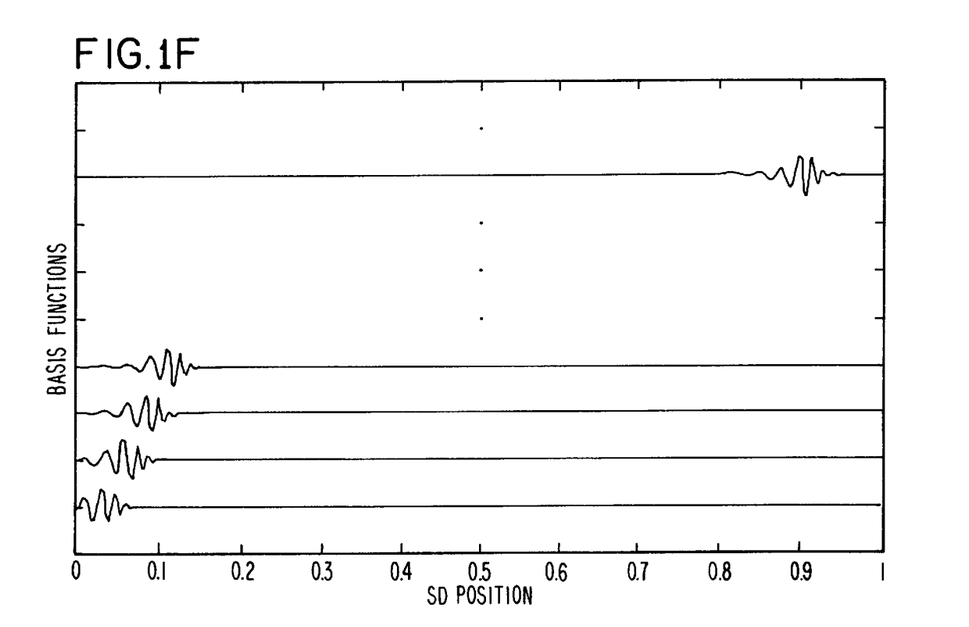

The biorthogonal wavelet bases include scaling bases illustrated in FIGS. 1A and 1C and detail bases illustrated in FIGS. 1B and 1D. In accordance with the properties of wavelet basis functions, once the set of scaling bases of FIG. 1A are selected, the remaining bases are fixed, i.e. the bases of FIGS. 1B–1D are determined from the bases of FIG. 1A. This is true for orthogonal bases also. In general, the integral of each of the scaling bases over the range thereof results in a normalized value of 1, while a similar integral for the detail functions results in a value of 0. Transformations using scaling bases result in scaled profiles which reflect portions of the measurement profile which can be corrected using CD actuators while transformations using detail bases reflect two-dimensional detail variations of the measurement profile which cannot be corrected using CD actuators. Thus, the scaling bases are best used for two-dimensional control of a process while detail bases are best used for analysis of the inherent machine characteristics of the profile. Results of transformations using detail basis functions can therefore be useful in identifying problems with the machine producing the web of material and suggesting how such machine problems can be corrected.

While a broad range of basis functions can be used for transformation purposes, it is currently preferred to use orthogonal or biorthogonal wavelet basis functions for the transformation. If biorthogonal wavelet bases are used, scaling bases of FIG. 1A are used for decomposition of a profile function and scaling bases of FIG. 1C are used for reconstruction. If orthogonal wavelet bases are used, the scaling bases of FIG. 1E are used for both decomposition and reconstruction of a profile function. The linear combination of basis functions is a powerful way to approximate any SD profile functions appearing in 2D sheet property variations. The coefficients in the linear combination of basis functions are called the functional representations of the given profile function and form a transformed variation expression. Although the given profile function can be a continuous function of the spatial variable x, the number of functional coefficients are finite.

In a general case, the basis functions may vary as the functions of both the temporal variable t and the spatial variable x. For practical purposes, basis functions are typically chosen to be independent of time t and generally correspond to fixed spatial locations, unless the basic spatial characteristics of the given 2D sheet variations are changing rapidly as a function of time t. It is believed that wavelet functions are well known to those skilled in the art; however, for additional information readers are referred to an article entitled Wavelet analysis by Bruce et al. in the October 1996 issue of IEEE Spectrum magazine and a book entitled *Wavelets and Filter Banks* by Gilbert Strang and Truong Nguyen published by Wellesley Cambridge Press in 1996 (ISBN 0961408871) which are incorporated by reference herein.

Assume that $b_i(x)$ for i=1,2,3, . . . , l represents a set of basis functions which completely span an l-dimensional space $R^l$, then the 2D sheet property variation y(x,t) or profile function can be transformed with the functional basis $b_i(x)$ using the equation:

$$y(x,t) = \sum_{i=1}^{l} a_i(t)b_i(x) + \epsilon(x,t) \tag{4}$$

where $a_i(t)$ for $i=1,2,3,\ldots,l$ are the functional coefficients of the 2D sheet property variation $y(x,t)$ or profile function and $\epsilon(x,t)$ is the residual that can not be transformed by the given set of basis functions.

Figure 2:
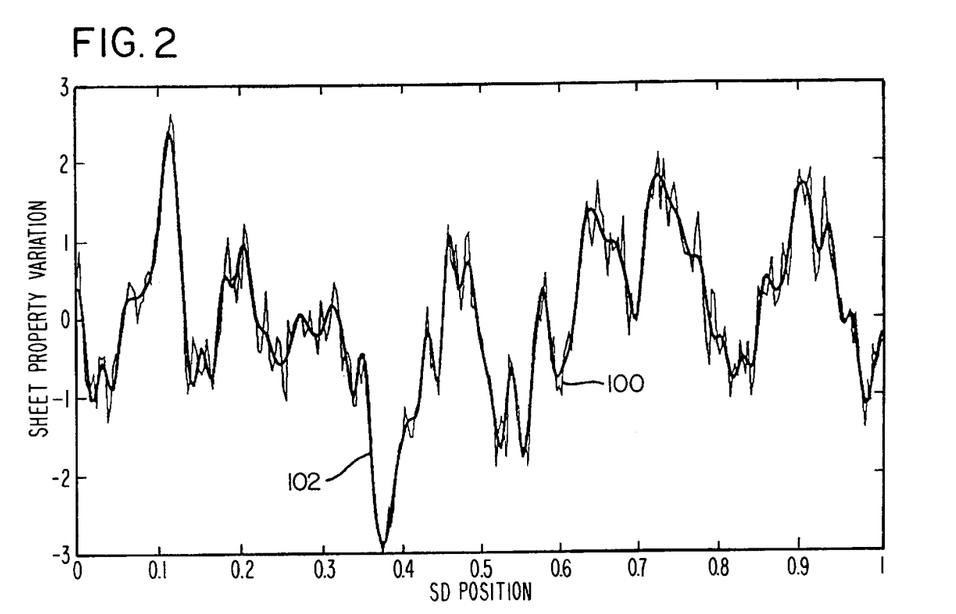
FIG. 2 shows a measured cross direction (CD) measurement function or profile and a reconstruction of the profile from a functional transformation of the profile using a linear combination of the sets of basis functions of FIGS. 1A and 1C.
Figure 3:
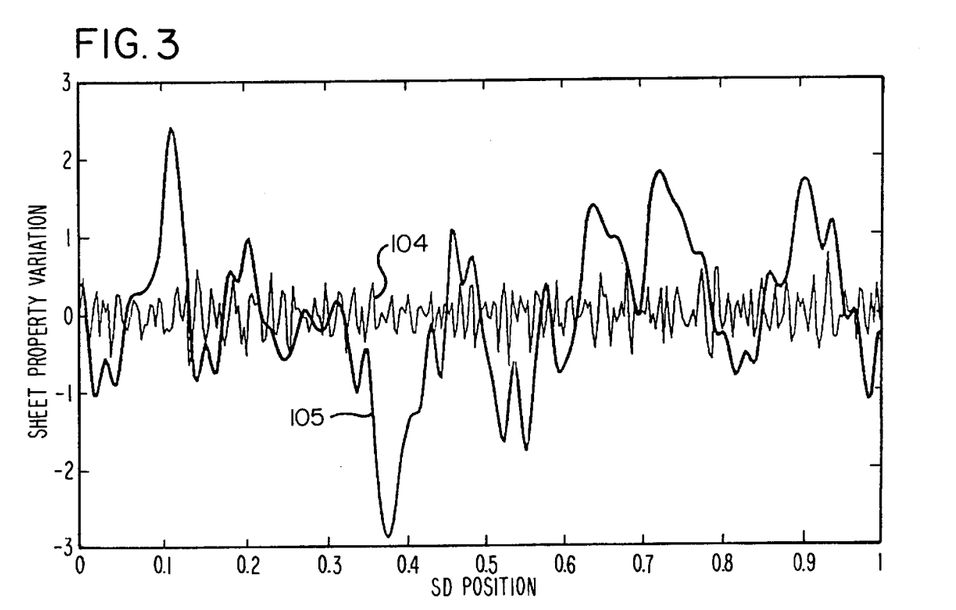
FIG. 3 illustrates the original measured CD profile of FIG. 2 and a residual profile, i.e. the portion of the original measured CD profile which can not be represented using the set of basis functions of FIGS. 1A and 1C.
Figure 4:
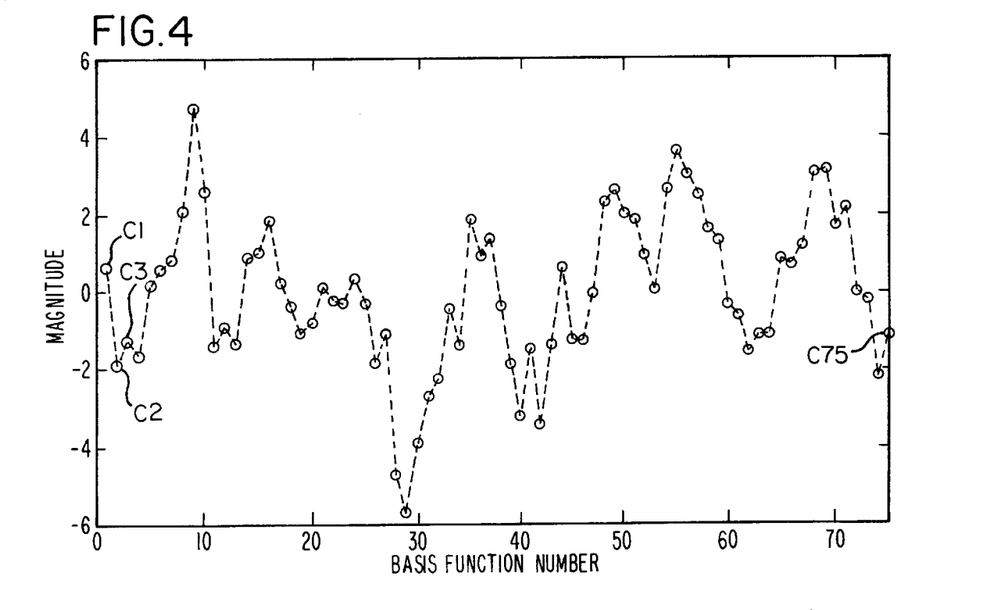
FIG. 4 illustrates the functional transformation or coefficients in the linear combination of the set of basis functions of FIG. 1C for the reconstruction of the profile of FIG. 2.

As mentioned above, FIGS. 1A–1D show sets of basis functions which span across the entire width of the web and can be used in the present invention. FIG. 2 shows a measured CD profile 100 or measurement function and its functional representation 102 derived from a linear combination of the basis functions of FIG. 1C. A residual profile 104 and a transformed profile 105 are shown in FIG. 3 and the coefficients C1, C2, C3, ... C75 of the transformation applied in FIG. 2 are shown in FIG. 4.

The basic requirement for a satisfactory transformation is that the residual component $\epsilon(x,t)$ has to be negligible. In other words, the norm of $\epsilon(x,t)$ should be small relative to the norm of $y(x,t)$, i.e. $\|\epsilon(x,t)\| \ll \|y(x,t)\|$. The coefficient array $a(t)=[a_1(t), a_2(t), \ldots, a_l(t)]^T$ can be viewed as a transformed or mapped profile of the original profile function $y(x,t)$ in an l-dimensional coordinate space spanned by the basis functions $b_i(x)$. Similarly, $y_c(x,t)$ and $y_r(x)$ can also be transformed in the same manner using the equations:

$$y_c(x,t) = \sum_{i=1}^{l} a_{ci}(t)b_i(x) + e_c(x,t) \tag{5}$$

$$y_r(x,t) = \sum_{i=1}^{l} a_{ri}(t)b_i(x) + e_r(x,t) \tag{6}$$

An advantage of the functional transformation of the invention of the present application is that for a given set of carefully selected basis functions $b_i(x)$, a profile function $y(x,t)$ can be expressed by a set of transform coefficients $a_i(t)$ which are functions of time t only and the number of transform coefficients, l, is finite and usually small. In other words, at any given time $t_k$, the continuous profile function $y(x,t_k)$ is represented by a finite number of coefficients $a_i(t_k)$ in the functional space specified by $b_i(x)$. From a data representation point of view, the set of coefficients $a_i(t_k)$ provides a compact representation for the given profile function $y(x,t_k)$.

For most practical applications, the above transformation will generally be implemented in a discrete computing environment such that both variables x and t have to be sampled and discretized. Assuming that the spatial variable x is divided into m spaces between the two edges of the web with $x_v$ representing the v-th discretized spatial location and that the temporal variable t is sampled every $\Delta t$ interval and the sampling time $t_k$ is simply indicated by the index k, the sheet property $p(x,t)$ is discretized as $p(v,k)$. The discretized expressions of equations (1) to (4) are:

$$p(k) = \frac{1}{m} \sum_{v=1}^{m} p(v,k) \tag{7}$$

$$y(k) = p(k) - p(k)1 \tag{8}$$

$$y(k) = y_c(k) + d(k) \tag{9}$$

$$y(k) = \sum_{i=1}^{l} a_i(k)b_i + \epsilon(k) = Ba(k) + \epsilon(k) \tag{10}$$

where $$B=[b_1, b_2, b_3, \ldots, b_l] \tag{11}$$

$$a(k)=[a_1(k), a_2(k), a_3(k), \ldots, a_l(k)]^T \tag{12}$$

where $[\ldots]^T$ represents the transpose of the vector $[\ldots]$ and $p(k)$, $y(k)$, $y_c(k)$, $d(k)$, $\epsilon(k)$, $b_i$, and 1 are discretized vectors of their corresponding functions in equations (1) to (4) with the dimension of m×1. With m usually being much larger than the number of basis functions needed to perform the functional transformation of a profile function. If the basis functions $b_i(x)$ are properly selected such that the residuals $\epsilon(k)$ are negligible, i.e. the norm of the vector $\epsilon(k)$ is much smaller than the norm of the profile vector $y(k)$, i.e. $\|\epsilon(k)\| \ll \|(k)\|$, and the inverse of $B^TB$ exists, then the transformed coefficients $a(k)$ can be obtained using the equation:

$$a(k)=(B^TB)^{-1}B^Ty(k)=\Gamma y(k) \tag{13}$$

where $$\Gamma=(B^TB)^{-1}B^T=[\gamma_1,\gamma_2,\ldots\gamma_l]^T \tag{14}$$

In the above equations, the basis functions $b_i$, which form matrix B, are called the "reconstruct basis" and the basis functions $\gamma_i$, which form matrix $\Gamma$, are called the "decomposition basis". Applicant of the present application discovered that the biorthogonal wavelet scaling functions or the orthogonal wavelet scaling functions fit nicely for $b_i$ and $\gamma_i$. This reflects the preferred form of practicing the present invention. That is, if a set of biorthogonal wavelet scaling functions, as shown in FIG. 1A, can be used for decomposing a profile function, then the corresponding set of biorthogonal wavelet scaling functions, as shown in FIG. 1C, can be used for reconstructing the profile. If a set of orthogonal wavelet scaling functions, as shown in FIG. 1E, is used, then this set of wavelet scaling functions can be used for both decomposition and reconstruction of a profile function. In the invention of the present application, either orthogonal or biorthogonal wavelet scaling functions are useful for performing profile functional transformation.

Similarly, the functional transformation for $y_c(k)$ and $y_r(k)$ can also be obtained using the equations:

$$y_c(k) = \sum_{i=1}^{l} a_{ci}(k)b_i + \epsilon_c(k) = Ba_c(k) + \epsilon_c(k) \tag{15}$$

$$y_r(k) = \sum_{i=1}^{l} a_{ri}(k)b_i + \epsilon_r(k) = Ba_r(k) + \epsilon_r(k) \tag{16}$$

$$a_c(k) = (B^TB)^{-1}B^Ty_c(k) = \Gamma y_c(k) \tag{17}$$

$$a_r(k) = (B^TB)^{-1}B^Ty_r(k) = \Gamma y_r(k) \tag{18}$$

Figure 9:
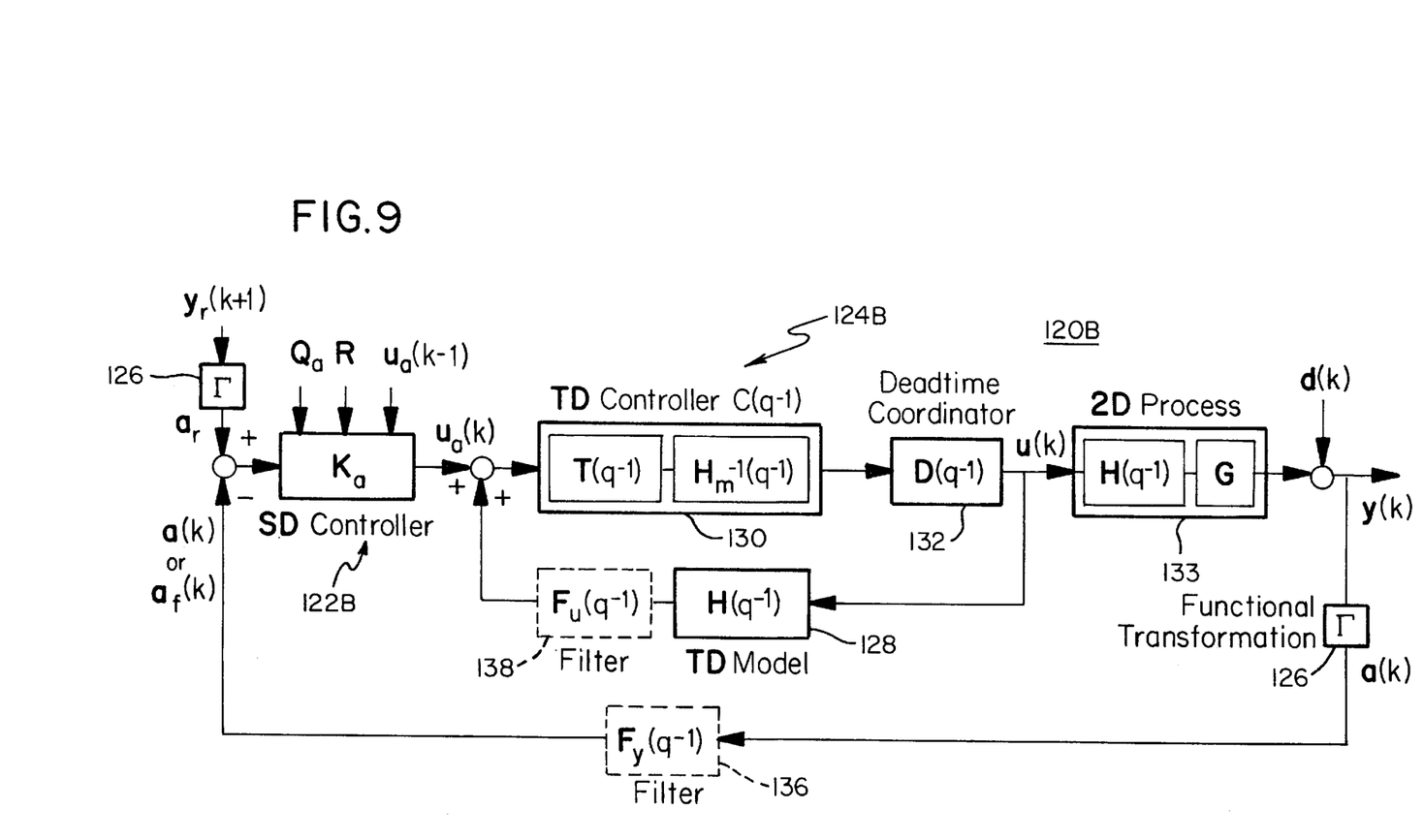
FIG. 9 shows an 2D variation controller with the functional transformation of the present application.

While many possible functional bases can be used as mentioned above, applicant has recognized that, for control purposes, the preferred basis functions are derived from the spatial response profiles of the CD actuators. As an example, the set of spatial response profiles themselves can be chosen as a set of basis functions. However, a set of wavelet scaling functions which closely approximate the set of spatial response profiles is currently preferred. The transformation of a profile function is performed by convoluting the profile function with the selected set of basis functions. The measured profile function $y(k)$ and the reference profile function $y_r(k+1)$ can be so processed as shown in FIG. 9. The transformation can be conveniently performed using a number of commercially available software packages including those mentioned in the referenced *Wavelet analysis* article in the October 1996 issue of IEEE Spectrum magazine.

Figure 5:
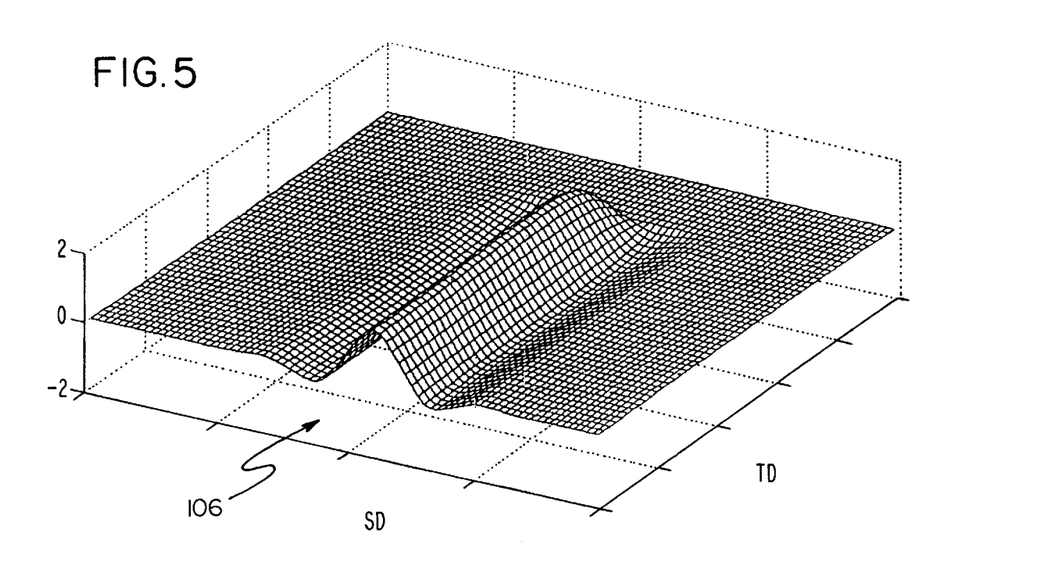
FIG. 5 shows a two-dimensional (2D) response from a control actuation of a CD actuator impacting a CD actuator zone illustrated as an entire SD profile function evolving simultaneously in the temporal direction.
Figure 6:
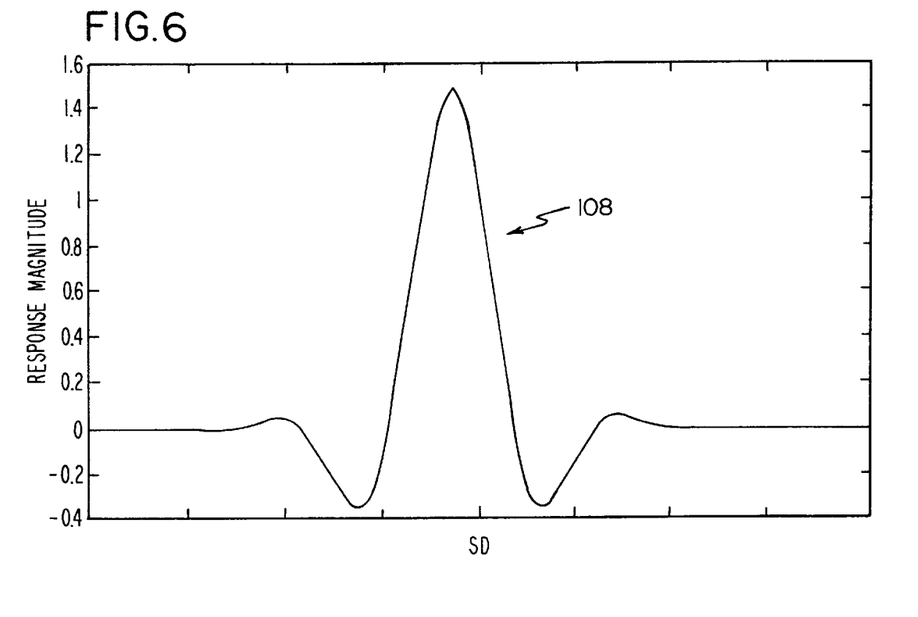
FIG. 6 illustrates an SD response of one CD actuator zone in a particular SD interval between two sheet edges having a particular response shape.
Figure 7:
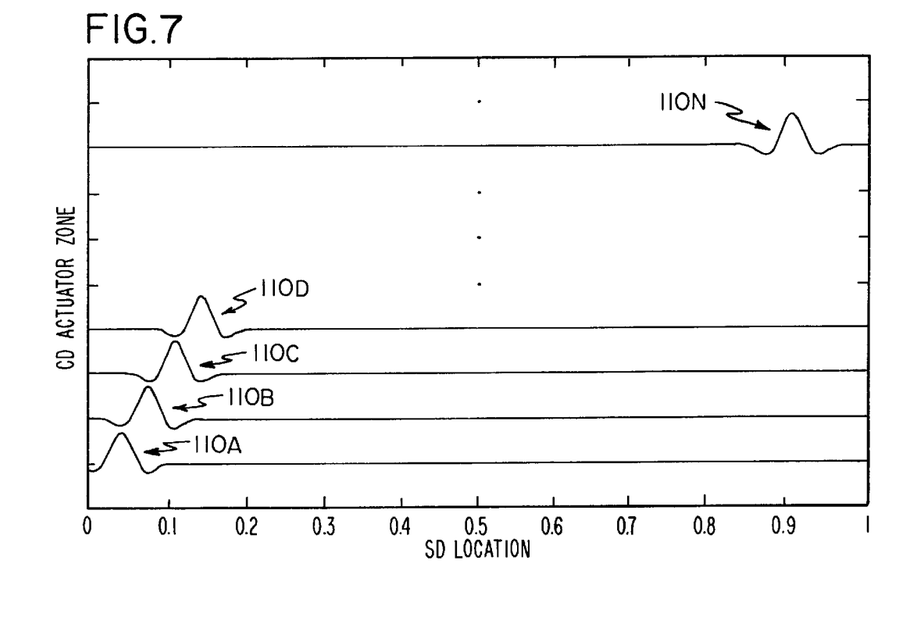
FIG. 7 illustrates a series of SD responses of n actuator zones viewed as a group of SD responses similar to the one of FIG. 6 with the SD responses appearing in the different corresponding SD locations across the web of material.

To control a 2D sheet property variation, the 2D responses from the control actions applied to the CD actuators need to be identified. A control action applied to each CD actuator causes the sheet property to change in both the temporal and the spatial directions for the corresponding actuator zone. The 2D response from the control action applied to a CD actuator can be seen as a spatial direction profile function 106 evolving simultaneously down in the temporal direction as shown in FIG. 5. The SD response of each CD actuator zone usually appears only in a particular SD interval between the two sheet edges. An example of a particular SD response shape 108 is illustrated in FIG. 6; however, the SD response of each CD actuator zone in the group of SD responses 110A–110N appears in a different SD location as shown in FIG. 7 and each SD response can have a slightly different shape and magnitude. The SD responses of the full-width CD actuator zones can be viewed as a group of SD responses 110A–110N.

The spatial direction response of the j-th CD actuator zone out of n actuators can be viewed as a profile function $g_j(x)$ or in the discrete form as a vector $g_j$ with the dimension of m×1. The temporal direction response of the j-th actuator zone can be represented by a transfer function $h_j(s)$ in the continuous domain or a discretized transfer function $h_j(q^{-1})$ in the discrete time interval where $q^{-1}$ represents a time-shift operator defined as:

$$q^{-1}y(k) \equiv y(k-1)$$

Both TD and SD responses of each CD actuator have to be identified through CD actuator tests, for example as described in U.S. Pat. No. 5,122,963 which is incorporated herein by reference.

Although the actual 2D process response from any CD actuator is continuous in both the SD and TD directions, the discrete representation will typically be used in a practical implementation. The discretized 2D sheet property response of an array of n CD actuator zones can be formulated in a multiple-input multiple-output (MIMO) matrix equation. As an example, the following equation can be used to characterize the 2D sheet property response between the actuator actions $u_c(k)$ and profile function $y_c(k)$:

$$y_c(k) = GH(q^{-1})u_c(k-1) \quad (19)$$

where G is an m×n matrix which contains all SD responses as:

$$G = [g_1, g_2, g_3, \ldots, g_n] \quad (20)$$

and H is an n×n diagonal matrix which contains all TD responses in its diagonal elements as:

$$H(q-1) = diag(h_1(q^{-1}), h_2(q^{-1}), h_3(q^{-1}), \ldots h_n(q^{-1})) \quad (21)$$

$$u_c(k) = [u_{c1}(k), u_{c2}(k), u_{c3}(k), \ldots, u_{cn}(k)]^T \quad (22)$$

$u_c(k)$ represents the incremental control actions applied to the full array of CD actuator at time k. The initial CD actuator setpoint profile is $u(0)=u_0$. The absolute setpoint profile u(k) for n CD actuators or actuator zones at time k is:

$$u(k) = u_c(k) + u(k-1) \quad (23)$$

At steady-state, the TD response $H(q^{-1})$ of all CD actuator zones in equation (19) is an identity matrix and the steady-state SD response of all CD actuator zones is represented by the G matrix. The SD response G as defined in equation (20), is an m by n matrix where m could be very large if the spatial variable x is sampled with a very fine resolution. If m is too large, the G matrix may become very inefficient for implementing a control arrangement for 2D sheet property variations. It is also important to note that the extra resolution with a large m actually does not make the extra fine variations more controllable. The controllability of a 2D profile is determined by the 2D responses, actuator spacing and control ranges of the CD actuators in the web-forming machine.

Applying the same functional transformation technique described above, the SD response of the j-th CD actuator zone can be transformed using the equations:

$$g_j = \sum_{i=1}^{l} \theta_{ji} b_i + \epsilon_{gj} = B\theta_j + \epsilon_{gj} \quad (24)$$

$$\theta_j = (B^T B)^{-1} B^T g_j = \Gamma g_j \quad (25)$$

where the B matrix is the same as that defined in equation (11). As mentioned above, the B matrix has to be properly selected so that the inverse of $B^T B$ exists and the residual $\epsilon_{gj}$ is negligible, i.e. $\|\epsilon_{gj}\| << \|g_j\|$, for SD responses of all CD actuator zones.

The full-width response gain matrix G can be transformed using:

$$G = B\Theta + \epsilon_G \quad (26)$$

and $$\Theta = (B^T B)^{-1} B^T G = \Gamma G \quad (27)$$

It is important to note that the set of basis functions $b_i$ should be chosen so that the residual $\epsilon_G$ is negligible relative to the full-width SD response gain matrix G. In other words, for control purposes, the basis functions which form matrix B should be derived from the SD response matrix G. Applicant has found that a series of wavelet scaling functions which are closely matched with the SD responses $g_i$ are preferred bases for transforming any profile functions. These wavelet scaling basis functions can be either orthogonal or biorthogonal. As some examples, the wavelet scaling functions associated with Haar wavelets, Daubechies wavelets, Symlets, biorthogonal wavelets and other similar wavelets are all suitable basis functions.

Combining equations (17), (19), and (27), the 2D full response model of a 2D sheet forming process is transformed into a functional space using the equation:

$$a_c(k) = \Theta H(q^{-1})u_c(k-1) \quad (28)$$

In equation (28), $a_c(k)$ is a vector with dimensions of l×1 and $\Theta$ is a matrix with dimensions of l×n where l is the number of basis functions used for performing functional transformation of profile functions. The number of basis functions l is usually much smaller than the number of discrete sampling points of profile functions m. Comparing equation (19) to equation (28), the primary difference is that the dimensions of $a_c(k)$ and $\Theta$ in equation (28) are much smaller than the dimensions of $y_c(k)$ and G in equation (19). Thus, equation (28) is a more efficient response model for dealing with a 2D sheet variation control problem. In the following description, a novel 2D variation control arrangement is derived based on either equation (19) or equation (28).

The 2D response models described in equation (19) and equation (28) show that the 2D variation control can be structured as an integration of two separate parts. One part focusing on the SD variation control and the other part focusing on the TD variation control. While the SD variation control is derived, the TD dynamics $H(q^{-1})$ is temporarily ignored or treated as an identity matrix. Similarly, while the TD variation control is formulated, the SD response is treated as a simple gain matrix. The 2D variations can be controlled with model predictive 2D variation controllers 120A, 120B illustrated in FIGS. 8 and 9, respectively. In the block diagrams of FIGS. 8 and 9, the controllers 120A, 120B are separated into optimal predictive SD variation controllers 122A, 122B and model based TD controllers 124A, 124B. The details of the formulations of the controllers 120A, 120B of FIGS. 8 and 9, respectively, are described below.

The goals of the optimal predictive SD variation controllers 122A, 122B are to minimize the difference between the predictive SD variation profile $\tilde{y}(k+1)$ and its target shape $y_r(k+1)$ subjected to all the required constraints on u(k). By momentarily ignoring the TD dynamics $H(q^{-1})$ in equation (19), the predictive SD variation profile $\tilde{y}(k+1)$ is defined as:

$$\tilde{y}(k+1) = Gu_c(k) + d(k) \tag{29}$$

where d(k) is the disturbance profile measured at time k. An optimal predictive SD variation predictive controller will generate a control action u(k) which minimizes the quadratic function J defined as:

$$J = (y_r(k+1) - \tilde{y}(k+1))^T Q(y_r(k+1) - \tilde{y}(k+1)) + u(k)^T Ru(k) \tag{30}$$

where Q is a weighting matrix for adjusting the relative weightings along the profile deviation $y_r(k+1) - \tilde{y}(k+1)$ and R is a weighting matrix for adjusting the relative weightings among the CD actuator setpoints u(k). The weighting matrix R is structured to ensure that the control setpoints meet all the required constraints for the control setpoint profile u(k).

In particular, the weighting matrix R is formed to have the following structure:

$$R = R_0 + D_1^T R_1 D_1 + D_2^T R_2 D_2 + \ldots \tag{31}$$

where $R_0, R_1, R_2, \ldots$ are diagonal matrices and $D_1, D_2, \ldots$ are band-diagonal matrices with proper dimensions. The matrices $R_0, R_1, R_2, \ldots$ and $D_1, D_2,$ are defined as:

$$R_0 = diag(r_{01}, r_{02}, \ldots, r_{0n}) \tag{32}$$

$$R_1 = diag(r_{11}, r_{12}, \ldots, r_{1(n-1)}) \tag{33}$$

$$R_2 = diag(r_{21}, r_{22}, \ldots, r_{2n}) \tag{34}$$

$$D_1 = \begin{bmatrix} 1 & -1 & 0 & 0 & \ldots & 0 \\ 0 & 1 & -1 & 0 & \ldots & 0 \\ 0 & 0 & 1 & -1 & \ldots & 0 \\ \ldots & \ldots & \ldots & \ldots & \ldots & \ldots \\ 0 & \ldots & \ldots & 1 & -1 & 0 \\ 0 & \ldots & \ldots & 0 & 1 & -1 \end{bmatrix}_{(n-1) \times n} \tag{35}$$

$$D_1 = \begin{bmatrix} 1 & -1 & 0 & 0 & \ldots & 0 \\ -1 & 2 & -1 & 0 & \ldots & 0 \\ 0 & -1 & 2 & -1 & \ldots & 0 \\ \ldots & \ldots & \ldots & \ldots & \ldots & \ldots \\ 0 & \ldots & 0 & -1 & 2 & -1 \\ 0 & \ldots & \ldots & 0 & -1 & 1 \end{bmatrix}_{n \times n} \tag{36}$$

With this structure for the weighting matrix R, each control setpoint can be assured of meeting the range limits by adjusting the weighting factors in $R_0$. Similarly, limits in the setpoint differences between adjacent CD actuator zones are met by adjusting the weighting factors in $R_1$ and the constraints on the second-order setpoint differences among the adjacent CD actuator zones will be achieved by adjusting weighting factors in $R_2$. As will be apparent to those skilled in the art, this structure for the weighting matrix R can be extended to satisfy higher-order constraints as required.

Ignoring the TD dynamics, i.e. $H(q^{-1})$ in equation (19), the SD optimal predictive control action $u_y(k)$ which minimizes the quadratic function J is:

$$u_y(k) = (R + G^T QG)^{-1} G^T Q(y_r(k+1) - y(k)) = K_y(y_r(k+1) - y(k)) \tag{37}$$

where $$K_y = (R + G^T QG)^{-1} G^T Q \tag{38}$$

and $$y(k) = y_c(k) + d(k) = Gu_c(k-1) + d(k) \tag{39}$$

As a special case, if the weighting matrix R=0 and the weighting matrix Q=I, then $K_y = (G^T G)^{-1} G^T$ which is the pseudo-inverse of the SD response gain matrix G and the optimal predictive control action is $u_y(k) = (G^T G)^{-1} G^T (y_r(k+1) - y(k))$. Generally speaking, the matrix $K_y$ defined in equation (38) can be viewed as a generalized pseudo-inverse of matrix G in conjunction with the weighting matrices R and Q. Matrix $K_y$ represents an optimal controller which maps the profile deviation $y_r(k+1) - y(k)$ into the control actions $u_y(k)$ according to equation (37).

If the transformed response model of equation (28) is used and the quadratic function to be minimized is defined as:

$$J_a = (a_r(k+1) - \tilde{a}(k+1))^T Q_a (a_r(k+1) - \tilde{a}(k+1)) + u(k)^T Ru(k) \tag{40}$$

where $\tilde{a}(k+1)$, $a(k)$, and $a_r(k+1)$ are the functional transforms of $\tilde{y}(k+1)$, y(k), and $y_r(k+1)$ respectively, the SD optimal predictive control actions which minimize the quadratic function $J_a$, is:

$$u_a(k) = (R + \Theta^T Q_a \Theta)^{-1} \Theta^T Q_a (a_r(k+1) - a(k)) = K_a(a_r(k+1) - a(k)) \tag{41}$$

where $$K_a = (R + \Theta^T Q_a \Theta)^{-1} \Theta^T Q_a \tag{42}$$

The optimal controller matrix $K_a$ is very similar to the controller matrix $K_y$.

The relationship between $u_a(k)$ and $u_y(k)$ can be obtained by substituting the functional transformation of equations (13)–(18) and (27) in equations (40) and (41). $J_a$ and $u_a(k)$ can be re-written as:

$$J_a = (y_r(k+1) - \tilde{y}(k+1))^T \Gamma^T Q_a \Gamma (y_r(k+1) - \tilde{y}(k+1)) + u(k)^T Ru(k) \tag{43}$$

and $$u_a(k) = (R + G^T \Gamma^T Q_a \Gamma G)^{-1} G^T \Gamma^T Q_a \Gamma (y_r(k+1) - y(k)) \tag{44}$$

Figure 8:
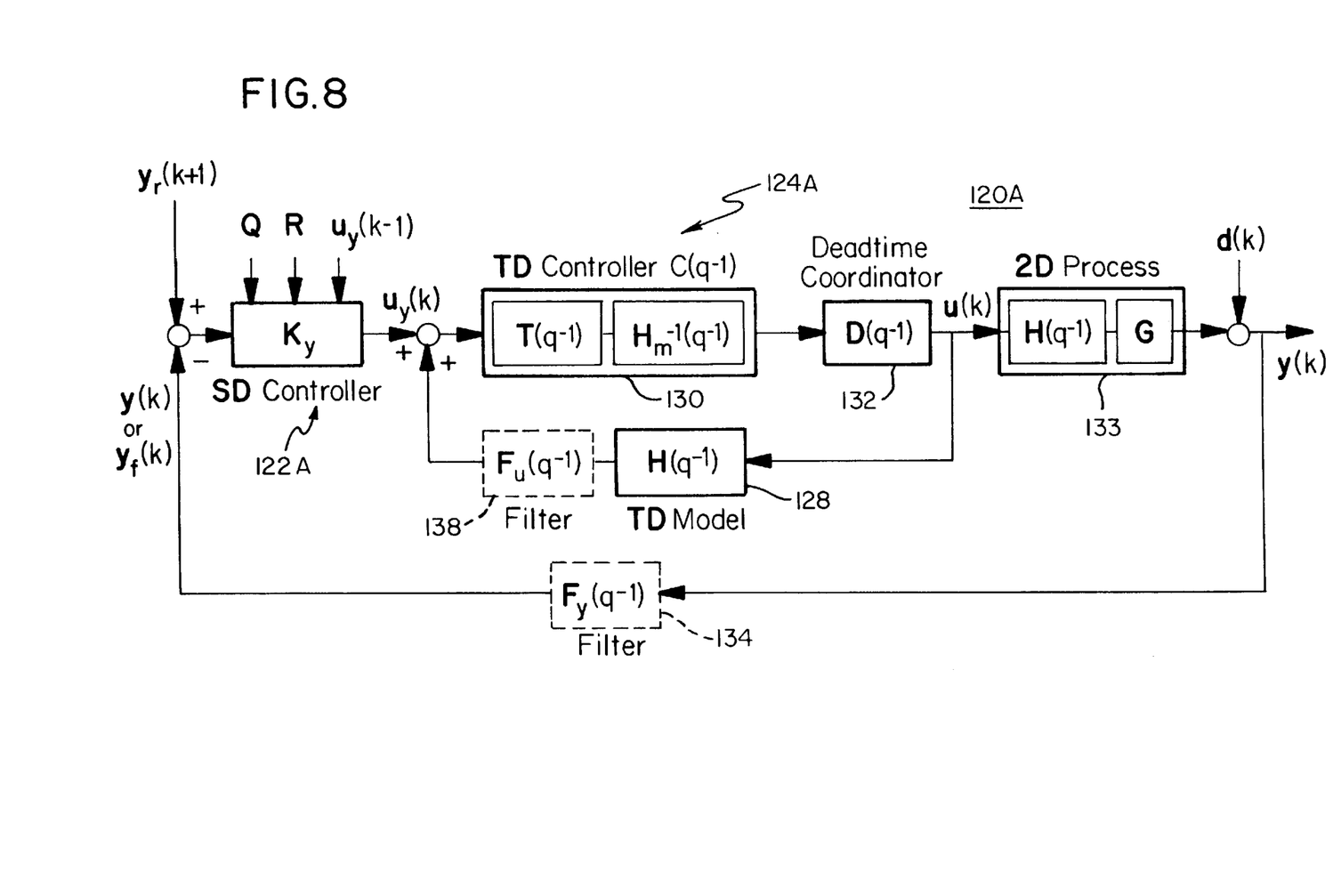
FIG. 8 shows an 2D variation controller without functional transformation.

In other words, if we let the weighting matrix Q in equation (30) be specifically selected as $Q = \Gamma^T Q_a \Gamma$, then $J_a$ in equation (43) is identical to J in equation (30) and $u_a(k)$ in equation (44) is identical to $u_y(k)$ in equation (37). Effectively, the functional transformation serves as a specific spatial filter which removes the higher-order or short wavelength spatial variations from the SD profiles. The SD controller with functional transformation is equivalent to a SD controller with a different weighting matrix applying on the SD profile deviation in the quadratic performance function. The solution $u_a(k)$ typically weights more heavily on the controllable low-order spectral variations in $y_r(k+1) - y(k)$. The described SD optimal predictive controller is a new SD control arrangement which can accommodate a broad range of profile representation. The block diagram of FIG. 8 shows the 2D variation controller 120A without functional transformation and the block diagram of FIG. 9 illustrates the 2D variation controller 120B with functional transformation. It is noted that the block diagrams of FIGS. 8 and 9 are for the 2D profile only, i.e. the pure machine direction (MD) variations are ignored as having been previously removed from the measured profile. The primary difference is that the transformation $\Gamma$ 126 is applied to both the discretized 2D profile function y(k) and the discretized reference profile function $y_r$ in the block diagram of FIG. 9 to produce a more efficient implementation.

The TD dynamics model $H(q^{-1})$ of 2D variations is handled with multivariable internal model predictive controllers 128 as shown in the block diagrams of FIGS. 8 and 9 which are identical for both implementations. Assuming that the minimum phase part of the TD response model is represented by a diagonal matrix $H_m(q^{-1})$ and the desirable closed-loop TD response dynamics are represented by a diagonal matrix $T_c(q^{-1})$, the internal model predictive controllers 128 are constructed as diagonal model predictive controllers using the equation:

$$T_c(q^{-1}) = diag(t_{c1}(q^{-1}), t_{c2}(q^{-1}), \ldots, t_{cn}(q^{-1})) \quad (45)$$

$$C(q^{-1}) = H_m^{-1}(q^{-1})T(q^{-1}) = diag(c_1(q^{-1}), c_2(q^{-1}) \ldots, c_n(q^{-1})) \quad (46)$$

where $$c_j(q^{-1}) = h_{mj}^{-1}(q^{-1})t_{cj}(q^{-1}) \quad (47)$$

As one example, the desirable closed-loop response can be defined as:

$$t_{cj}(s) = \frac{1}{\tau_c s + 1} \quad (48)$$

As a part of the internal model predictive control structure, the TD dynamic model $H(q^{-1})$ is implemented as a positive feedback which wraps around the TD controllers $C(q^{-1})$ 130 as shown in the block diagrams of FIGS. 8 and 9. The steady-state response of the desirable closed-loop TD response $T_c(q^{-1})$ has to be an identity matrix T(1)=I. With T(1)=I, the inner loops in the block diagrams of FIGS. 8 and 9 inherently exhibit the integral control action for its outer control loop. Depending on the tuning applied to the TD controllers 130, an extra anti-windup logic can also be incorporated in the inner control loop to handle actuator constraints for aggressive dynamic control actions as will be apparent to those skilled in the art.

The non-minimum phase part of the TD dynamics, such as the transport delays, can be unified by a deadtime delay coordinator, $D(q^{-1})$ 132 which makes the delay times encountered by all the CD actuator zones the same. The control actions sent to the CD actuators, i.e. the 2D process 133, are coordinated by $D(q^{-1})$ and $C(q^{-1})$ in such a way that all actuator zones appear to have the same delay and same closed-loop dynamics.

The feedback filters $F_y(q^{-1})$ 134 or $F_a(q^{-1})$ 136 and Fu(q-1) 138 can also be used in the controllers 120A, 120B of the block diagrams of FIGS. 8 and 9 to gain two-degrees of freedom controllability. Each of filters $F_y(q^1)$ 134, $F_a(q^{-1})$ 136 and $F_u(q^{-1})$ 138 can be a diagonal matrix with a simple low-order or a lead-lag estimator as defined in:

$$F_y(q^{-1}) = diag(f_{y1}(q^{-1}), f_{y2}(q^{-1}), \ldots, f_{ym}(q^{-1})) \quad (49)$$

$$F_u(q^{-1}) = diag(f_{u1}(q^{-1}), f_{u2}(q^{-1}), \ldots, f_{un}(q^{-1})) \quad (50)$$

$$F_a(q^{-1}) = diag(f_{a1}(q^{-1}), f_{a2}(q^{-1}), \ldots, f_{ul}(q^{-1})) \quad (51)$$

As one example, the filter can be defined as:

$$f_{yi}(s) = f_{ui}(s) = f_{ai}(s) = \frac{1}{\tau_f s + 1} \text{ or } \frac{\tau_c s + 1}{\tau_f s + 1} \quad (52)$$

where the time constants $\tau_f$ in these filters should be determined from the spectral contents of the 2D variability in the web of material being produced as is well known in the art.

The desirable closed-loop time constants $\tau_c$ in $T_c(q^{-1})$ and $\tau_f$ in $F_y(q^{-1})$, $F_a(q^{-1})$ and $F_u(q^{-1})$ are the key control tuning parameters for the TD controllers. These time constants can be adjusted for different conditions. If the higher frequency TD direction disturbance appears in the measurement, the longer filter time constant $\tau_f$ can be used. If a substantial deviation occurs as a step change, a shorter $\tau_c$ should be used and if the predicted response deviates from the actual response, then a longer $\tau_c$ and $\tau_f$ should be tuned. The tuning parameters $\tau_c$ and $\tau_f$ are determined by the combination of all the above factors to achieve the desirable closed-loop responses is for different 2D variability conditions.

Advantages of the new 2D modeling and control arrangements described above include:

1. A true two-dimensional variability is modeled. 2D variability is explicitly represented by its spatial direction variation and temporal direction variation.

2. A generalized functional representation is introduced. The basis functions are derived from the SD response of CD actuator control actions. The wavelet scaling basis functions are found to be preferred bases for the functional representations of 2D sheet variation profiles. The compact representation, which can minimize the memory and real-time requirements, is efficient for actual implementations.

3. The optimal predictive SD control arrangement focuses the controllable spectrum of 2D profile variations. The uncontrollable high order spatial variation is separated from the controllable component by the generalized functional transformation.

4. The described method unifies existing CD control arrangements. By selecting different basis functions, existing CD control arrangements can be derived as special cases under the described framework.

5. The model-based predictive TD controller and the adaptive tuning adaptive tuning arrangement are incorporated to achieve different closed-loop responses for different process conditions. Recognizing the special characteristics of 2D process disturbances and the fidelity of the response model, the desirable closed-loop and TD feedback filter time constants can be adjusted dynamically.

Having thus described the invention of the present application in detail and by reference to preferred embodiments thereof, it will be apparent that modifications and variations are possible without departing from the scope of the invention defined in the appended claims.

What is claimed is:

1. A method for determining a two-dimensional variation for a web of material as said web of material is being manufactured, said method comprising the steps of:

measuring at least one characteristic of said web substantially across an entire width of said web to generate a two-dimensional measurement function;

selecting a series of wavelet basis functions; and convoluting said two-dimensional measurement function with said wavelet basis functions to generate a two-dimensional variation signal representative of said web of material.

2. A method for determining a two-dimensional variation for a web of material as said web of material is being manufactured as claimed in claim 1 wherein the step of selecting a series of wavelet basis functions comprises the steps of:

determining a plurality of response profiles generated in response to individual actuations of a corresponding plurality of CD actuators used in a machine performing said method; and deriving said series of wavelet basis functions from said plurality of response profiles.

3. A method for determining a two-dimensional variation for a web of material as said web of material is being manufactured as claimed in claim 1 wherein the step of selecting said series of wavelet basis functions comprises the steps of:

determining a plurality of response profiles generated in response to individual actuations of a corresponding plurality of CD actuators used in a machine performing said method; and selecting said series of wavelet basis functions to closely match said plurality of response profiles.

4. A method for determining a two-dimensional variation for a web of material as said web of material is being manufactured along a machine direction, said method comprising the steps of:

measuring at least one characteristic of said web of material as a function of the cross machine direction of said web of material to generate a measurement function;

determining variation in the machine direction of the web of material which variation is substantially independent of the cross machine direction to generate a pure machine direction function;

separating the pure machine direction function from the measurement function to generate a two-dimensional sheet variation function; and using wavelet basis functions to transform said two-dimensional sheet variation function into a two-dimensional variation signal representative of said web of material.

5. A method for determining a two-dimensional variation for a web of material as said web of material is being manufactured along a machine direction as claimed in claim 4 wherein said step of separating the pure machine direction function from the measurement function comprises the step of subtracting said pure machine direction function from said measurement function.

6. A method for determining a two-dimensional variation for a web of material as said web of material is being manufactured along a machine direction as claimed in claim 4 wherein said step of using wavelet basis functions to transform said two-dimensional sheet variation function into a two-dimensional variation signal comprises the steps of:

selecting a series of wavelet basis functions; and convoluting said two-dimensional sheet variation function with said wavelet basis functions.

7. A method for controlling a two-dimensional variation for a web of material as said web of material is being manufactured, said method comprising the steps of:

measuring at least one characteristic of said web substantially across an entire width of said web to generate a measurement function;

determining a two-dimensional measurement function from said measurement function;

transforming said two-dimensional measurement function to generate a transformed variation expression representative of said web of material;

determining a reference profile function;

transforming said reference profile function to generate a transformed reference expression representative of said reference profile function;

subtracting said transformed variation expression from said transformed reference expression to generate a first input signal for a spatial direction controller;

generating a spatial direction control signal in response to said first input signal;

combining said spatial direction control signal with a modeled temporal direction feedback signal to generate a second input signal for a temporal direction controller;

generating a two-dimensional process control signal in response to said second input signal; and coordinating deadtime delays to unify delay times among a series of cross direction actuators to generate a process control signal from said two-dimensional process control signal.

8. A method for controlling a two-dimensional variation for a web of material as said web of material is being manufactured as claimed in claim 7 further comprising the step of configuring said spatial direction controller to be an optimal predictive spatial direction controller.

9. A method for controlling a two-dimensional variation for a web of material as said web of material is being manufactured as claimed in claim 7 wherein said step of transforming said measurement function to generate a transformed variation expression representative of said web of material comprises the steps of:

selecting a series of wavelet scaling basis functions; and convoluting said two-dimensional measurement function with said wavelet scaling basis functions.

10. A method for controlling a two-dimensional variation for a web of material as said web of material is being manufactured as claimed in claim 9 wherein said step of selecting a series of wavelet scaling basis functions comprises the steps of:

determining response profiles generated in response to actuations of CD actuators used in a machine performing said method; and deriving said series of wavelet scaling basis functions from said response profiles.

11. A method for controlling a two-dimensional variation for a web of material as said web of material is being manufactured as claimed in claim 10 wherein said step of transforming said reference profile function to generate a transformed reference expression representative of said profile function comprises the step of convoluting said reference profile function with said series of wavelet scaling basis functions.

12. A method for controlling a two-dimensional variation of a web of paper as said web of paper is being manufactured by a paper making machine having a headbox actuator, said method comprising the steps of:

measuring at least one characteristic of said web substantially across an entire width thereof to generate a measurement function;

determining machine direction variations contained within said measurement function;

removing said machine direction variations from said measurement function to generate a two-dimensional variation signal including both cross directional and residual variations; and controlling said headbox actuator in response to said two-dimensional variation signal.

13. A method for controlling a two-dimensional variation of a web of paper as said web of paper is being manufactured by a paper making machine having a headbox actuator as claimed in claim 12 wherein said step of controlling said headbox actuator comprises the step of controlling a slice lip of said headbox.

14. A method for controlling a two-dimensional variation of a web of paper as said web of paper is being manufactured by a paper making machine having a headbox actuator as claimed in claim 12 wherein said step of controlling said headbox actuator comprises the step of controlling a dilution valve of said headbox.

15. A method for controlling a two-dimensional variation of a web of paper as said web of paper is being manufactured by a paper making machine having a headbox actuator as claimed in claim 12 further comprising the steps of:

transforming said two-dimensional measurement function to generate a transformed variation expression representative of said web of material;

determining a reference profile function;

transforming said reference profile function to generate a transformed reference expression representative of said reference profile function;

combining said transformed variation expression and said transformed reference expression to generate a first input signal for a spatial direction controller;

generating a spatial direction control signal in response to said first input signal;

combining said spatial direction control signal with a modeled temporal direction feedback signal to generate a second input signal for a temporal direction controller;

generating a two-dimensional process control signal in response to said second input signal; and coordinating a deadtime delay to unify delay times among a series of cross direction actuators to generate a process control signal from said two-dimensional process control signal.

16. A method for controlling a two-dimensional variation of a web of paper as said web of paper is being manufactured by a paper making machine having a headbox actuator as claimed in claim 15 wherein said temporal direction controller includes an adjustable closed-loop time constant and said method further comprises the steps of:

filtering said two-dimensional measurement function with a filter having an adjustable filter time constant;

filtering said modeled temporal direction feedback signal with a filter having an adjustable filter time constant; and adjusting said adjustable filter time constants and said adjustable closed-loop time constant to control two degrees of freedom of two-dimensional variation control of said method, said adjustable time constant for filtering said two-dimensional measurement function and said adjustable time constant for filtering said temporal direction feedback signal being equal to each other.

17. A method for controlling a two-dimensional variation of a web of paper as said web of paper is being manufactured by a paper making machine having a headbox actuator as claimed in claim 16 wherein said step of adjusting said adjustable filter time constants and said adjustable closed-loop time constant comprises the steps of:

adjusting said filter time constants to adapt said method to different two-dimensional variations; and adjusting said closed-loop time constant to adapt said method to changes of said reference profile function.

18. A method for controlling a two-dimensional variation of a web of material as said web of material is being manufactured by a machine having a cross direction controller, said method comprising the steps of:

measuring at least one characteristic of said web substantially across an entire width of said web to generate a measurement function;

determining machine direction variations contained within said measurement function;

removing said machine direction variations from said measurement function to generate a two-dimensional variation signal including both cross directional variations and residual variations; and controlling said cross direction controller in response to said two-dimensional variation signal.

19. A method for controlling a two-dimensional variation of a web of paper as said web of paper is being manufactured by a paper making machine having a headbox actuator as claimed in claim 18 further comprising the steps of:

transforming said two-dimensional measurement function to generate a transformed variation expression representative of said web of material;

determining a reference profile function;

transforming said reference profile function to generate a transformed reference expression representative of said reference profile function;

combining said transformed variation expression and said transformed reference expression to generate a first input signal for a spatial direction controller;

generating a spatial direction control signal in response to said first input signal;

combining said spatial direction control signal with a modeled temporal direction feedback signal to generate a second input signal for a temporal direction controller;

generating a two-dimensional process control signal in response to said second input signal; and coordinating a deadtime delay to unify delay times among a series of cross direction actuators to generate a process control signal from said two-dimensional process control signal for controlling said cross direction controller.

20. A method for controlling a two-dimensional variation for a web of material as said web of material is being manufactured as claimed in claim 19 further comprising the step of configuring said spatial direction controller to include a weighting matrix for adjusting the relative weightings among the actuator setpoints of said cross direction controller to be an optimal predictive spatial direction controller.

21. A method for controlling a two-dimensional variation for a web of material as said web of material is being manufactured as claimed in claim 20 further comprising the step of configuring said optimal predictive spatial direction controller to generate a control action u(k) which minimizes the quadratic function J defined by the equation $$J=(y_r(k+1)-\bar{y}(k+1))^T Q(y_r(k+1)-\bar{y}(k+1))+u(k)^T Ru(k).$$

22. A method for controlling a two-dimensional variation for a web of material as said web of material is being manufactured as claimed in claim 20 further comprising the step of forming said weighting matrix to have a structure defined by the equation $R=R_0+D_1^T R_1 D_1+D_2^T R_2 D_2+ \ldots$ where $R_0, R_1, R_2, \ldots$ are diagonal matrices and $D_1, D_2, \ldots$ are band-diagonal matrices with proper dimensions.

23. A method for controlling a two-dimensional variation for a web of material as said web of material is being manufactured as claimed in claim 22 further comprising the steps of selecting $R_0, R_1, R_2$ to provide different order of constraints for individual actuators of said cross direction controller.

24. A method for controlling a two-dimensional variation of a web of material as said web of material is being manufactured by a machine having a cross direction controller as claimed in claim 18 wherein said step of controlling said cross direction controller comprises the steps of:

selecting a series of wavelet basis functions; and decomposing said two-dimensional variation signal with said basis functions.

25. A method for controlling a two-dimensional variation of a web of material as said web of material is being manufactured by a machine having a cross direction controller as claimed in claim 24 wherein the step of selecting a series of basis functions comprises the step of selecting said basis functions to be wavelet scaling basis functions.

* * * * *